(12) United States Patent
Judd et al.

(10) Patent No.: US 7,957,788 B2
(45) Date of Patent: Jun. 7, 2011

(54) INTERVENTIONAL MAGNETIC RESONANCE IMAGING BASED ON GLOBAL COHERENT FREE PRECESSION

(75) Inventors: Robert M. Judd, Durham, NC (US); Wolfgang G. Rehwald, Durham, NC (US); Raymond J. Kim, Durham, NC (US)

(73) Assignee: Duke University, Durham, NC (US)

( * ) Notice: Subject to any disclaimer, the term of this patent is extended or adjusted under 35 U.S.C. 154(b) by 1740 days.

(21) Appl. No.: 11/047,685

(22) Filed: Feb. 2, 2005

(65) Prior Publication Data

US 2006/0184007 A1    Aug. 17, 2006

(51) Int. Cl.
*A61B 5/05*    (2006.01)
*G01V 3/00*    (2006.01)

(52) U.S. Cl. ........ 600/423; 600/410; 600/419; 324/309; 324/313

(58) Field of Classification Search .................. 600/410, 600/419–420, 423; 324/306–307, 309, 318–319
See application file for complete search history.

(56) References Cited

U.S. PATENT DOCUMENTS

| | | | |
|---|---|---|---|
| 5,337,749 A * | 8/1994 | Shimizu | 600/419 |
| 6,683,454 B2 | 1/2004 | Rehwald et al. | |
| 6,806,709 B2 * | 10/2004 | Markl et al. | 324/309 |
| 6,814,280 B2 * | 11/2004 | Miyoshi et al. | 324/319 |
| 7,254,436 B2 * | 8/2007 | Judd et al. | 600/410 |
| 7,579,834 B2 * | 8/2009 | Yui | 324/307 |
| 2004/0039278 A1 * | 2/2004 | Wacker et al. | 600/410 |
| 2004/0113613 A1 * | 6/2004 | Markl et al. | 324/306 |
| 2004/0204643 A1 * | 10/2004 | Jesmanowicz | 600/410 |
| 2004/0254452 A1 * | 12/2004 | Judd et al. | 600/419 |
| 2005/0054914 A1 * | 3/2005 | Duerk et al. | 600/423 |

OTHER PUBLICATIONS

Heart Disease and Stroke Statistics—2004 Update, American Heart Association, pp. 1-48.
Aspelin et al, "Nephrotoxic Effects in High-Risk Patients Undergoing Angiography", The New England Journal of Medicine, vol. 348, No. 6, Feb. 6, 2003, pp. 491-499.
Guttman et al, "Real-Time Accelerated Interactive MRI with Adaptive TSENSE and UNFOLD", Magnetic Resonance in Medicine, 50:315-321, 2003, pp. 315-321.
Lederman et al, "Catheter-Based Endomyocardial Injection with Real-Time Magnetic Resonance Imaging", Circulation, Mar. 19, 2002, pp. 1282-1284.

(Continued)

*Primary Examiner* — Long V Le
*Assistant Examiner* — Angela M Hoffa
(74) *Attorney, Agent, or Firm* — Nixon & Vanderhye P.C.

(57) ABSTRACT

Methods and systems for obtaining intravascular magnetic resonance images of blood flow are disclosed. In preferred forms, a train of radio frequency (RF) pulses is produced by an intravascularly introduced RF transmitter positioned in proximate location to the blood flow so as to create a continuous stream of coherently excited protons of the blood flow. The coherently excited protons of the blood flow are sampled as the protons freely precess while flowing through a region of three dimensional space unaffected by the ongoing intravascular RF excitation. An image of the sampled coherently excited protons may then be constructed.

11 Claims, 3 Drawing Sheets

OTHER PUBLICATIONS

Rickers et al, "Magnetic Resonance Imaging Guided Cardiovascular Interventions in Congenital Heart Disease", Journal of Interventional Cardiology, vol. 16, No. 2, 2003, pp. 143-147.

Susil et al, "Multifunctional Interventional Devices for MRI: A Combined Electrophysiology/MRI Catheter", Magnetic Resonance in Medicine, 47:594-600, 2002.

Guttman et al, "Techniques for Fast Stereoscopic MRI", Magnetic Resonance in Medicine, 46-317-323, 2001. Rickers et al, "Magnetic Resonance Image-Guided Transcatheter Closure of Atrial Septal Defects", Circulation, Jan. 7/14, 2003, pp. 132-138.

Rehwald et al, "Noninvasive cineangiography by magnetic resonance global coherent free precession", Nature Medicine, vol. 10, No. 5, May 2004, pp. 1-5.

Stefansic et al, "Effects of Acceleration, Jerk and Field Inhomogeneities on Vesel Positions in Magnetic Resonance Angiography", MRM 40-261-271, 1998.

Frank et al, "Elimination of Oblique Flow Artifacts in Magnetic Resonance Imaging", Magnetic Resonance in Medicine, 25, 299-307, 1992.

Thunberg et al, "Correction for Acceleration-Induced Displacement Artifacts in Phase Contrast Imaging", Magnetic Resonance in Medicine, 43:734-738, 2000.

* cited by examiner

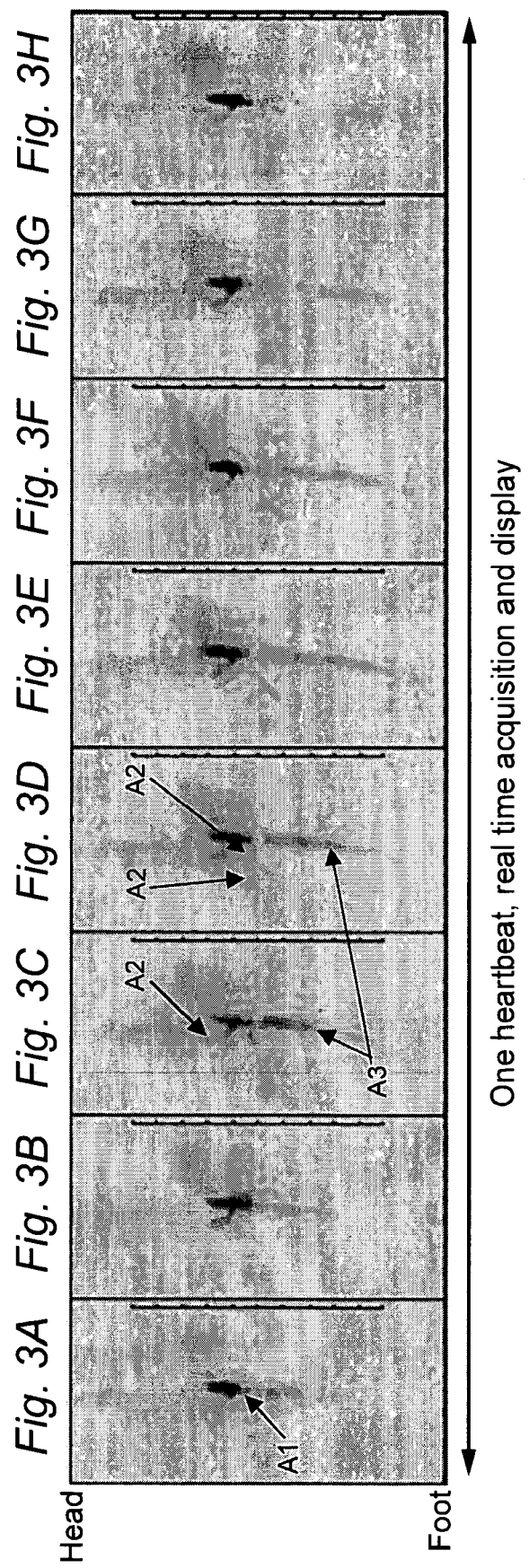

INTERVENTIONAL MAGNETIC RESONANCE IMAGING BASED ON GLOBAL COHERENT FREE PRECESSION

FIELD

The present invention relates generally to magnetic resonance imaging (MRI). More particularly, the present invention relates to MRI methods and systems whereby spatially-selective excitation is achieved by intravascularly locating a radio frequency (RF) transmitter, most preferably by means of an intravascular catheter.

BACKGROUND

A recent study by the American Heart Association has noted that cardiovascular diseases, such as heart attacks and strokes, are the leading cause of death in the Western world. Traditionally, x-ray angiography has been the primary method of diagnosing the presence and significance of arterial stenoses, the underlying cause of cardiovascular disease. In the United States alone over 1.4 million diagnostic x-ray angiography procedures are performed each year. In addition to diagnostic x-ray angiography, widely-used interventions such as percutaneous transluminal coronary angioplasty (PTCA) are performed under x-ray angiographic guidance. Accordingly, x-ray angiography is by far the most widely used technique to diagnose and treat cardiovascular disease.

While extremely useful, x-ray angiography involves ionizing radiation and requires contrast agents which are known to cause renal injury. (See, Aspelin et al, Nephrotoxic Effects in High-Risk Patients Undergoing Angiography. *New England Journal of Medicine*. 348(6): 491-99, the entire content of which is expressly incorporated hereinto by reference.) Therefore, an alternative approach to x-ray angiography which does not involve contrast agents or ionizing radiation is desirable.

In this regard, magnetic resonance imaging (MRI) is a well known diagnostic technique that does not rely on ionizing radiation and has thus been proposed as an alternative to x-ray angiography. Existing interventional MRI techniques, however, are characterized by slow movie frame rates, poor spatial resolution, and the need to track the complex 3-dimensional location of catheters using traditional 2-dimensional MR images. To date, interventional MRI has not achieved clinical application.

A new class of magnetic resonance images has recently been described which is based on a previously unrecognized spin state known as global coherent free precession (GCFP). (See, Rehwald et al. Non-Invasive Cine Angiography by Magnetic Resonance Global Coherent Free Precession, *Nature Medicine* 2004; 10(5), and U.S. patent application Ser. No. 10/449,252 filed on May 30, 2003, the entire content of each being expressly incorporated hereinto by reference.) The use of GCFP allows the acquisition of images depicting blood flow. In brief summary, protons within moving blood are "tagged" every few milliseconds as the blood flows through a slice in space. Simultaneously, previously tagged blood is maintained in the GCFP state which allows acquisition of consecutive movie frames as the heart pushes blood out of the excitation slice. Body tissue surrounding the moving blood is never excited and therefore remains invisible. The processes used to "tag" blood as it flows through the slice are the traditional combinations of radiofrequency (RF) and gradient waveforms to achieve spatially-selective proton excitation.

SUMMARY

Broadly, the present invention is embodied in the recognition that the GCFP state can also be created by the use of an invasive catheter acting as an RF transmitter. More specifically, spatially-selective excitation is achieved according to the present invention by virtue of the physical intravascular location of the RF catheter tip within the body instead of the use of traditional RF and gradient waveforms. According to the present invention, therefore, when catheter-based RF transmission is combined with a MRI pulse sequence creating the GCFP state, protons in blood flowing past the catheter tip are locally excited and continue to produce an MRI signal even after they flow far from the catheter tip and into downstream blood vessels. All body tissue surrounding this flowing blood, conversely, is never excited and therefore remains invisible.

In practice, the overall effect of the interventional GCFP (hereinafter sometimes referenced as "IGCFP") approach according to the present invention is that, for the first time, images can be produced which are virtually identical to those of x-ray angiography performed with a continuous infusion of an x-ray contrast agent. The excited blood flowing past the catheter tip and into downstream blood vessels can be imaged as rapidly as 30 frames per second, providing real-time visualization of pulsating blood and catheter tip location as the physician advances the catheter into target blood vessels. Importantly, because catheter-based RF excitation does not excite body tissue which surrounds the flowing blood, projection images can be acquired which eliminates the need to track the catheter tip by traditional two-dimensional MRI. These IGCFP projection images allow the physician to perform catheter-based interventions in a manner directly analogous to x-ray angiography. The MRI approach, however, eliminates the need for nephrotoxic contrast agents and ionizing radiation associated with x-ray angiography.

These and other aspects and advantages will become more apparent after careful consideration is given to the following detailed description of the preferred exemplary embodiments thereof.

BRIEF DESCRIPTION

Reference will hereinafter be made to the accompanying drawings, wherein;

FIGS. 3a-3h are a collection of representative in vivo images obtained according to the Example below.

DETAILED DESCRIPTION OF THE INVENTION

According to the present invention the condition of global coherent free precession may be combined with a catheter-based RF excitation. In the setting of GCFP, the MRI signal associated with locally excited protons can be globally sampled repeatedly and non-destructively as the protons travel through three-dimensional (3D) space, even in the absence of additional RF excitation. In this regard, GCFP can occur provided that two fundamental conditions are met, namely that (1) RF excitation must remain in phase with previous excitations for moving protons; and (2) the magnetic field gradients required for imaging must not cause the excited protons to accumulate phase shifts as they move through 3D space.

Importantly, in practice these GCFP conditions can be met while simultaneously achieving two additional goals. Firstly, RF excitation pulses can be played every few milliseconds alternating with playing the GCFP gradients, so that RF excitation and reading of the GCFP signal occurs quasi simultaneously, effectively creating a continuous outward flow of excited protons. Secondly, the MRI signal can be sampled and used to construct projection images analogous to those of x-ray angiography using the same gradient waveforms employed for RF excitation and GCFP. Taken collectively, therefore, a train of RF pulses produces a continuous stream of coherently excited protons whose signal is continuously sampled as they freely precess while arbitrarily flowing through regions of three dimensional space not affected by the ongoing RF excitation.

Figure 1:
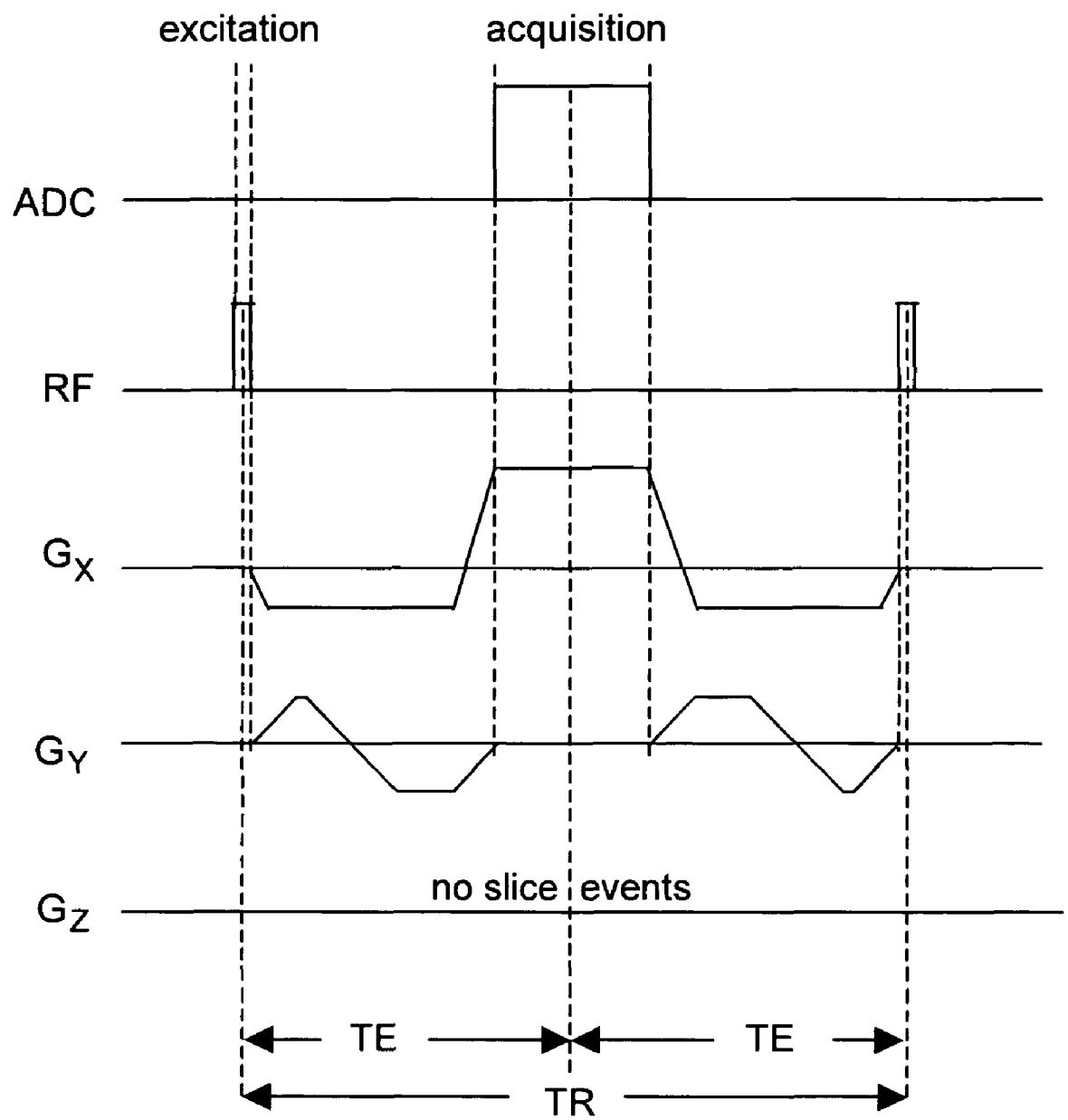
FIG. 1 is a timing diagram for an interventional MRI pulse sequence in accordance with the present invention.

FIG. 1 shows a presently preferred timing diagram for an interventional MRI pulse sequence whose gradient waveforms satisfy the second GCFP condition for stationary spins and for those moving at constant velocity (zero- and first-order gradient moments are zero). (See, Stefansic et al, Effects of Acceleration, Jerk, and Field Inhomogeneities on Vessel Positions in Magnetic Resonance angiography. *Magnetic Resonance in Medicine* 1998; 40; 261-271, Frank et al, Elimination of Oblique Flow Artifacts in Magnetic Resonance Imaging, *Magnetic Resonance in Medicine* 1992; 25; 299-307, and Thunberg et al, correction for Acceleration-induced Displacement Artifacts in Phase Contrast Imaging, *Magnetic Resonance in Medicine* 2000; 43; 734-738, the entire content of each being expressly incorporated hereinto by reference.) Specifically, the area under each gradient waveform equals zero at the center of the echo and at the end of TR, and the first moment of each gradient waveform equals zero at the end of TR. Zero zeroth order and first order moments are required to ensure that a state of free precession occurs for both stationary spins and for spins moving at constant velocity. Nulling of higher-order moments such as second order moments to be insensitive towards acceleration can be included if desired. The first GCFP condition can be achieved by setting the frequency of the RF transmitter exactly on resonance and setting the phase increment of the transmitter to zero.

Importantly, the RF excitation in FIG. 1 is non-selective. Spatial selectivity using traditional MRI approaches is not needed according to the present invention because spatial selection is achieved using the catheter tip as the RF transmitter. Because no spatially-selective gradient waveforms are required, a shorter TR and therefore a faster image frame rate can be achieved.

The present invention will be further understood by reference to the following non-limiting example.

Example

The pulse sequence shown in FIG. 1 was developed and tested on a routine clinical 1.5T MRI scanner (Siemens Sonata, Siemens Medical Systems, Erlangen, Germany) equipped with state-of-the-art gradient coils (isotropic, 40 mT/m maximum gradient, 200 mT/m/ms slew rate) and an eight-channel phased array RF receiver.

Figure 2:
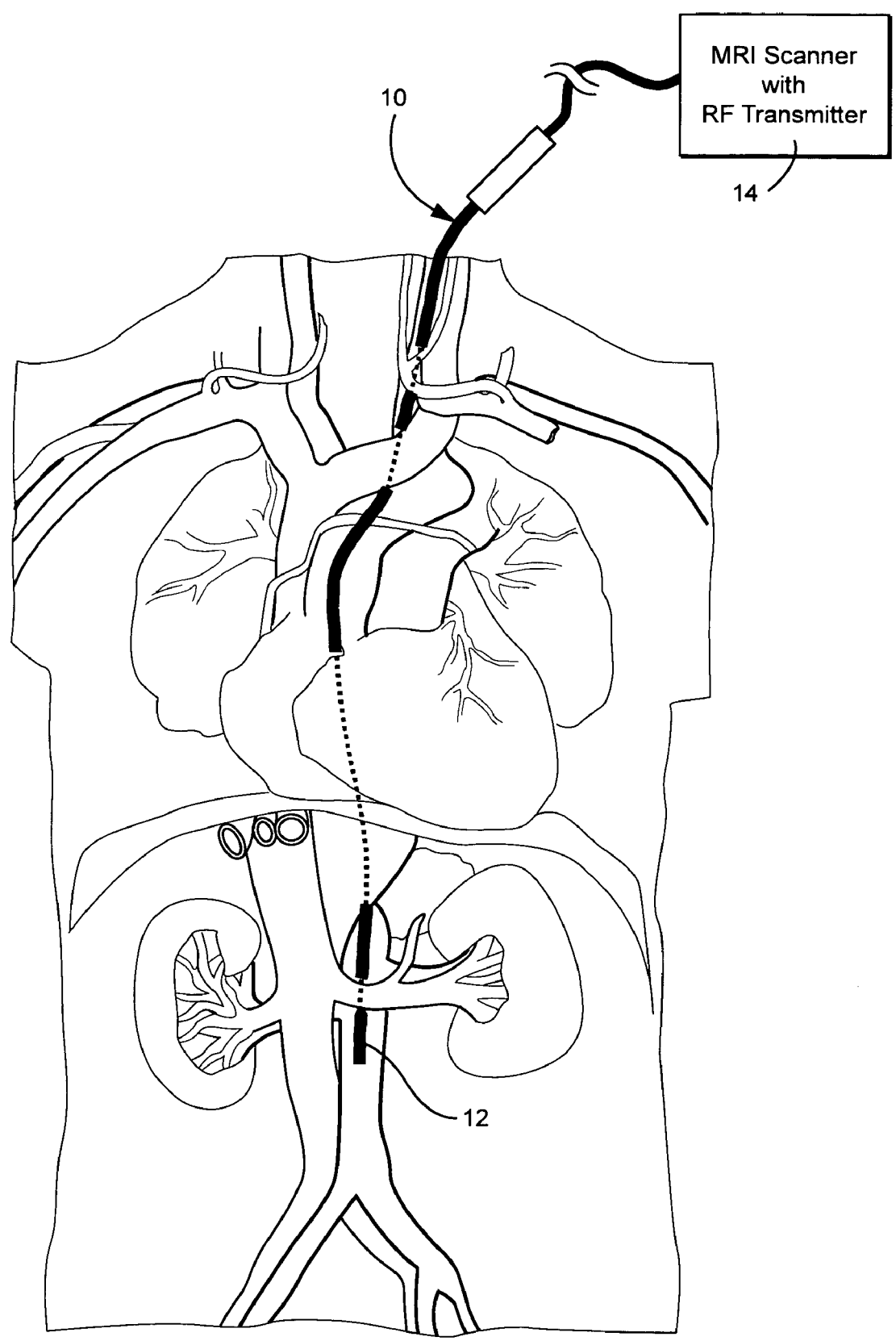
FIG. 2 is a schematic representation of the placement of an RF catheter to obtain in vivo images according to the Example below.

In vivo images were acquired in anesthetized dogs. FIG. 2 schematically shows the experimental preparation. In this regard, an RF transmit catheter 10 having an RF transmitter at its distal end 12 was constructed and interfaced to the MRI scanner 14. The RF transmit catheter 10 was introduced into the carotid artery using standard interventional techniques. Real-time images were then acquired at 30 frames per second as the catheter was advanced forward into the descending aorta.

FIGS. 3a-3h show representative images obtained in this Example. In this regard, the catheter tip is clearly visible in FIG. 3A and identified by arrow A1. As heart contraction begins (FIG. 3B), blood is physically pushed into and fills the side branches (i.e., descending aorta as well as celiac renal and superior mesenteric arteries) as shown in FIGS. 3C-3D and identified by arrows A2 and A3. Thereafter, heart relaxation (FIGS. 3E through 3H) ultimately results in blood no longer visibly filling such side branches.

It will therefore be observed from FIGS. 3A-3H that, as the heart contracts and pushes blood forward, spins passing the catheter tip are excited and continue to yield signal even after flowing far from the catheter and into branch vessels (e.g., superior mesenteric and renal arteries).

As will now be appreciated, the presence of signal far from the catheter tip is made possible by the current invention. The ability to directly visualize both blood flow and catheter tip location in three-dimensional space in real time without a contrast agent or ionizing radiation is expected to have wide clinical application.

Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for obtaining magnetic resonance images of flowing blood in a vascular vessel comprising:
   (a) positioning a radio frequency (RF) transmitter in the vascular vessel,
   (b) conducting global coherent free precession (GCFP) magnetic resonance imaging (MRI) of blood flowing intravascularly in the vessel by operating the RF transmitter within the vascular vessel; and
   (c) obtaining images of the flowing blood.

2. A method as in claim 1, wherein (b) comprises operating the RF transmitter at a frequency which is exactly on resonance and at a zero phase increment.

3. A method as in claim 1 or 2, wherein (b) comprises operating a MRI timing sequence which prevents magnetic field gradients required for imaging from causing excited protons to accumulate phase shifts as the protons move through three dimensional space.

4. A method of obtaining intravascular magnetic resonance images (MRI) of blood flow comprising:
   (a) intravascularly positioning a radio frequency (RF) transmitter in proximity to the blood flow,
   (b) causing the RF transmitter to produce a train of RF pulses so as to form a continuous stream of coherently excited protons of the blood flow,
   (c) performing global coherent free precession (GCFP) magnetic resonance imaging (MRI) by continuously sampling the coherently excited protons of the blood flow as the protons freely precess while flowing through a region of three dimensional space unaffected by the ongoing RF excitation, and
   (d) generating an image of the sampled coherently excited protons.

5. A method as in claim 4, wherein step (a) further comprises providing an intravascular catheter having a RF transmitter at a distal end thereof.

6. A method as in claim 4 or 5, which comprises operating a MRI timing sequence which prevents magnetic field gradients required for imaging from causing excited protons to accumulate phase shifts as the protons move through three dimensional space.

7. A system for obtaining magnetic resonance images of flowing blood in a vascular vessel comprising:
   a catheter having a radio frequency (RF) transmitter at a distal end thereof configured to be positioned in the vascular vessel,
   a magnetic resonance data acquisition and imaging system configured to conduct global coherent free precession (GCFP) magnetic resonance imaging (MRI) of blood flowing intravascularly in the vessel and obtain images thereof, wherein
   the RF transmitter is configured to produce a train of RF pulses so as to form a continuous stream of coherently excited protons of the blood flow within the vascular vessel during operation of the data acquisition and imaging system so that images of the flowing blood therein are obtained.

8. A system as in claim 7, wherein the RF transmitter is configured to operate at a frequency which is exactly on resonance and at a zero phase increment.

9. A system as in claim 7 or 8, wherein the RF transmitter and the data acquisition and imaging system are configured to operate to achieve a MRI timing sequence which prevents magnetic field gradients required for imaging from causing excited protons to accumulate phase shifts as the protons move through three dimensional space.

10. A system for obtaining intravascular magnetic resonance images of blood flow comprising:
   (a) a catheter having an RF transmitter at a distal end thereof configured to produce a train of radio frequency (RF) pulses so as to form a continuous stream of coherently excited protons of the blood flow, and
   (b) a data acquisition and imaging system configured to conduct global coherent free precession (GCFP) magnetic resonance imaging (MRI) by continuously sampling the coherently excited protons of the blood flow as the protons freely precess while flowing through a region of three dimensional space unaffected by the ongoing RF excitation and further configured to generate an image thereof.

11. A system as in claim 10, wherein said RF transmitter and said data acquisition and imaging system are configured to operate to achieve a MRI timing sequence which prevents magnetic field gradients required for imaging from causing excited protons to accumulate phase shifts as the protons move through three dimensional space.

* * * * *